United States Patent [19]
Bohannon et al.

[11] Patent Number: 5,792,654
[45] Date of Patent: Aug. 11, 1998

[54] MICROORGANISM CULTURE TRAY

[75] Inventors: Lon Maynard Bohannon, Lansing, Mich.; Raymond Louis Miller, Lindenwold; Sudhakar Vulimiri, Gibbstown, both of N.J.

[73] Assignee: Neogen Corporation, Lansing, Mich.

[21] Appl. No.: 967,512

[22] Filed: Nov. 11, 1997

Related U.S. Application Data

[63] Continuation-in-part of Ser. No. 70,591, May 12, 1997.

[51] Int. Cl.$^6$ .............................. C12M 3/00; B65D 51/18
[52] U.S. Cl. .............................. 435/305.3; 435/305.4; 422/102; 220/253
[58] Field of Search .............. 435/288.3, 288.4, 435/305.1, 305.2, 305.3, 305.4; 422/102; 220/253, 796, DIG. 13; 222/572

[56] References Cited

U.S. PATENT DOCUMENTS

| | | |
|---|---|---|
| D. 316,752 | 5/1991 | Ricketts. |
| 3,356,462 | 12/1967 | Cooke et al. . |
| 3,649,464 | 3/1972 | Freeman . |
| 4,240,751 | 12/1980 | Linnecke et al. . |
| 4,292,273 | 9/1981 | Butz et al. . |
| 4,495,289 | 1/1985 | Lyman et al. . |
| 4,545,958 | 10/1985 | Dopatka . |
| 4,560,535 | 12/1985 | Bouchee . |
| 4,735,778 | 4/1988 | Maruyama et al. . |
| 4,741,619 | 5/1988 | Humphries et al. . |
| 4,761,378 | 8/1988 | Godsey . |
| 5,462,860 | 10/1995 | Mach . |
| 5,508,005 | 4/1996 | Mathus . |
| 5,540,891 | 7/1996 | Portmann et al. . |
| 5,547,112 | 8/1996 | Schiffer ........................... 222/571 |
| 5,587,321 | 12/1996 | Smith et al. . |
| 5,601,998 | 2/1997 | Mach et al. . |
| 5,700,655 | 12/1997 | Croteau et al. ................... 435/30 |

FOREIGN PATENT DOCUMENTS

WO 91/09970 of 0000 WIPO .
WO 97/18455 of 0000 WIPO .

*Primary Examiner*—David A. Redding
*Attorney, Agent, or Firm*—Ian C. McLeod

[57] ABSTRACT

A microorganism culture tray (10) including a cover (11) and base (12) are described. The base and cover have polygonal preferably hexagonal, walls (14, 15) which allow the cover to be mounted on the base either opening a recess (17) or closing the recess.

11 Claims, 5 Drawing Sheets

MICROORGANISM CULTURE TRAY

This application is a continuation-in-part of copending application Ser. No. 29/070,591 filed on May 12, 1997.

BACKGROUND OF THE INVENTION

SUMMARY OF THE INVENTION

The present invention relates to a microorganism culture tray. The tray includes polygonal walls on an integral base and an integral cover so that a recess in the walls can be exposed or covered for removal of excess culture medium from the tray.

DESCRIPTION OF RELATED ART

The related art in multiwell trays is described in U.S. Pat. No. Des. 316,752 to Ricketts, U.S. Pat. No. 3,356,462 to Cooke et al., U.S. Pat. No. 3,649,464 to Freeman, U.S. Pat. No. 4,240,751 to Linnecke et al., U.S. Pat. No. 4,292,273 to Butz et al, U.S. Pat. No. 4,495,289 to Lyman et al., U.S. Pat. No. 4,545,958 to Dopatka, U.S. Pat. No. 4,560,535 to Bouchée, U.S. Pat. No. 4,735,778 to Maruyama et al., U.S. Pat. No. 4,741,619 to Humphries et al., U.S. Pat. No. 4,761,378 to Godsey, U.S. Pat. No. 5,462,860 to Mach, U.S. Pat. No. 5,508,005 to Mathus, U.S. Pat. No. 5,540,891 to Portmann et al., U.S. Pat. No. 5,587,321 to Smith, et al., U.S. Pat. No. 5,601,998 to Mach et al. Also WO 97/18455 to Croteau et al and WO 91/09970 to Willingham et al describe culture trays. None of these trays have a recess in a base for draining the culture medium while leaving culture medium in the wells or with a cover which can be positioned to open and then to close the recess. Such a construction would greatly facilitate the use of the tray for microorganism culturing.

OBJECTS

It is therefore an object of the present invention to provide a tray with a recess and cover for opening and closing the recess. It is further an object of the present invention to provide a tray which is very economical to produce and which greatly facilitates culturing of the microorganisms. These and other objects will become increasingly apparent by reference to the following description and the drawings.

DESCRIPTION OF PREFERRED EMBODIMENTS

The present invention relates to a microorganism culture tray which comprises: (a) an integral base with (i) a planar surface having multiple concentric circular rows of wells around a longitudinal axis for containing a liquid culture medium and the microorganisms, (ii) a first wall projecting from the planar surface above the wells around the axis with flat portions, (iii) a second regular polygonal wall with flat portions connected to the first wall to form an inverted V intersection above the wells and planar surface and extending below the planar surface below the wells, and (iv) an outwardly extending flange from the second wall upon which the base rests; and (v) a recess in both of the walls at intersections of two of the flat portions of the walls which allows the liquid culture medium to be drained from the planar surface when the planar surface is tilted at an angle less than 90°; and (b) a transparent integral transparent cover having flat portions defining a wall of the cover conforming to the second wall of the base wherein an intersection of two of the flat portions of the cover define an opening which exposes the recess when the cover is in one position and covers the recess when the cover is in another position on the base. Preferably the polygonal wall is hexagonal.

Figure 1:
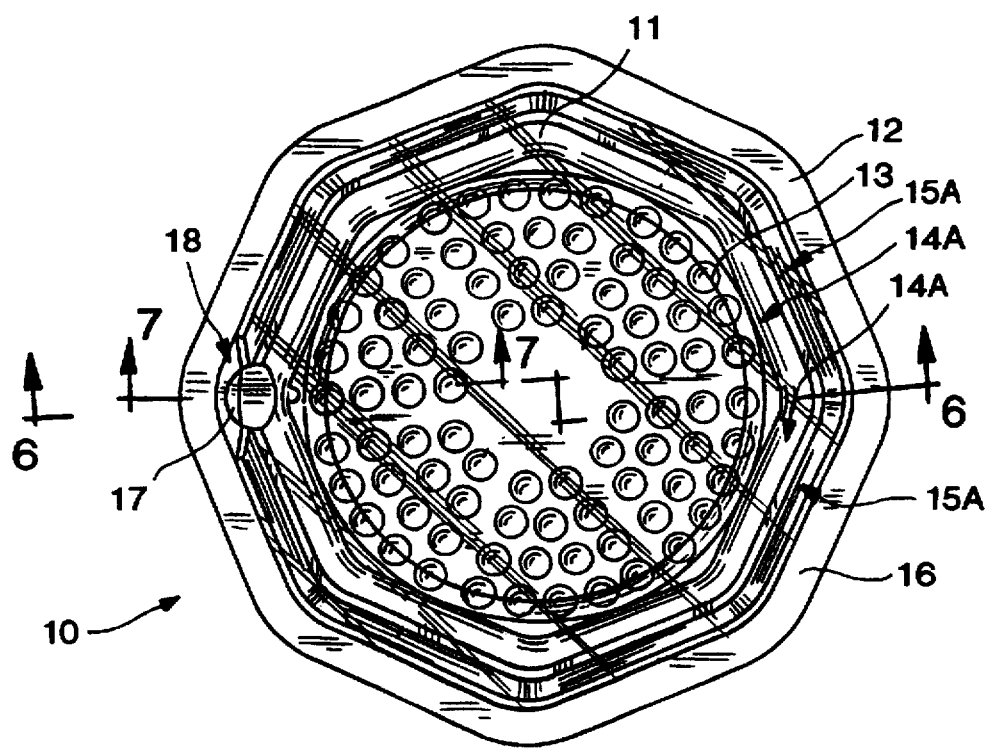
FIG. 1 is a plan view of a cover 11 and base 12 forming the tray 10 of the present invention.
Figure 2:
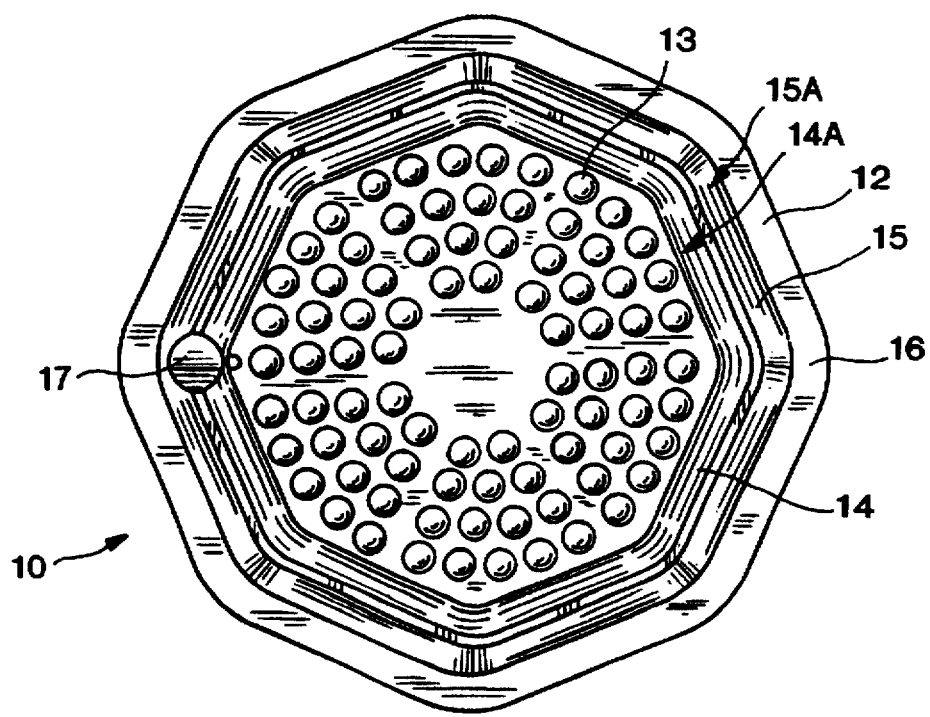
FIG. 2 is a plan view of the base 12 alone, as shown in FIG. 1.
Figure 3:
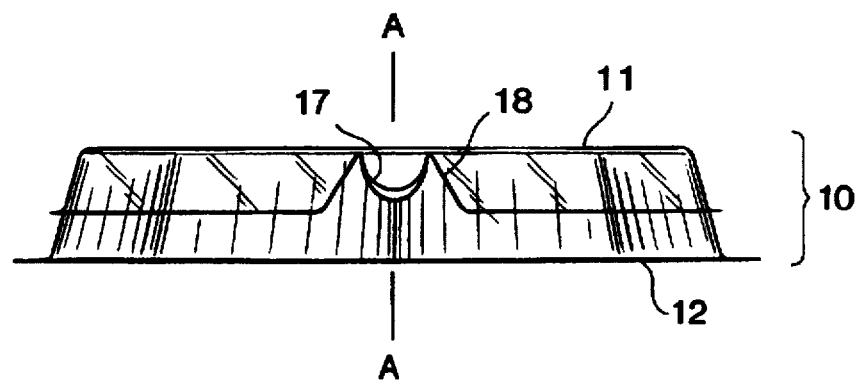
FIG. 3 is a front view of the tray 10 including the cover 11 and the base 12 showing the recess 17 in the base 12 and the opening 18 in the cover 11.
Figure 4:
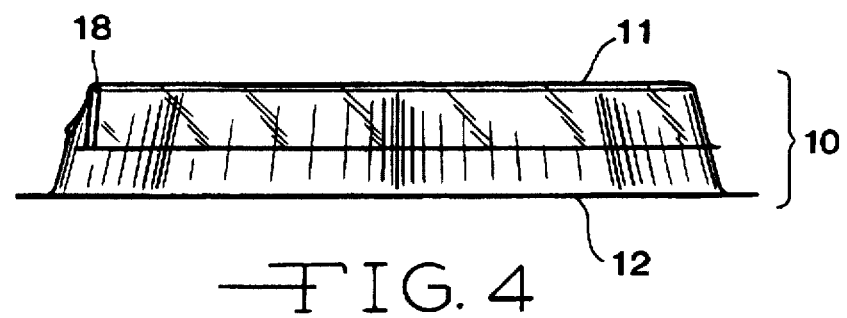
FIG. 4 is a side view of the tray 10 as shown in FIG. 3.
Figure 5:
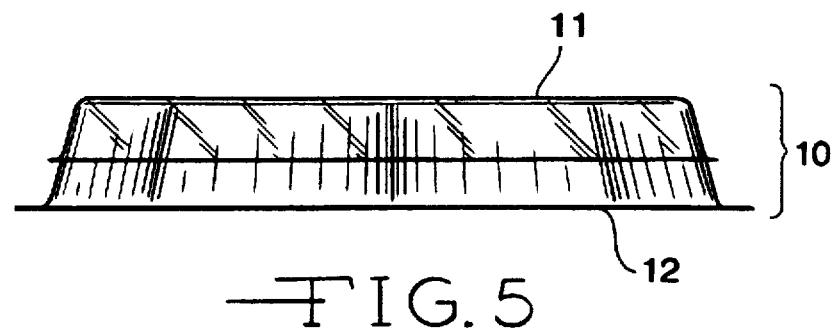
FIG. 5 is a rear view of the tray 10 shown in FIG. 3.
Figure 6:
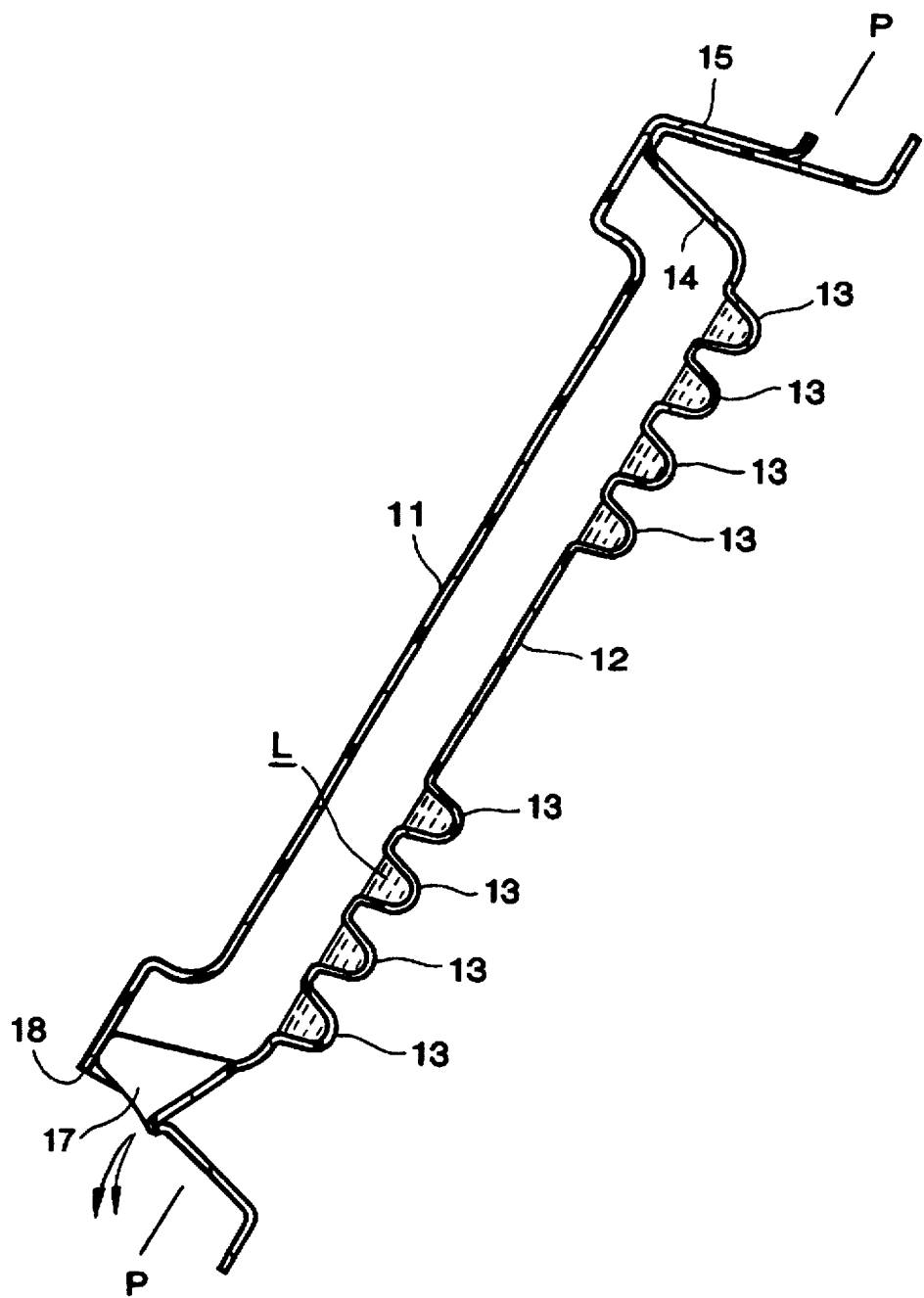
FIG. 6 is a cross-sectional view along line 6—6 of FIG. 1 showing the cover 11, base 12, wells 13, recess 17 and opening 18.
Figure 7:
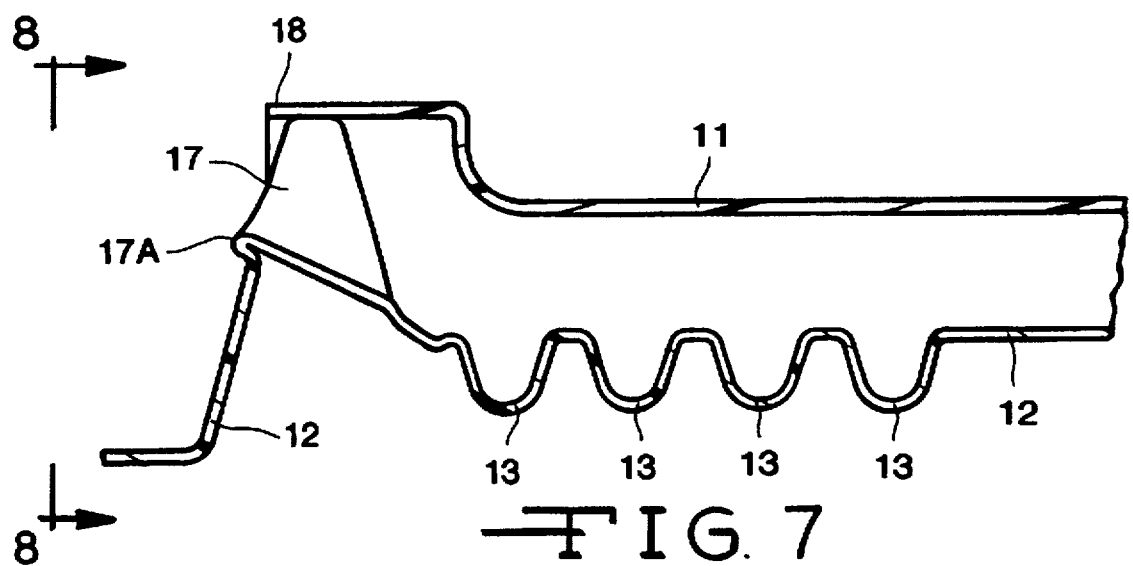
FIG. 7 is a partially enlarged cross-sectional view of FIG. 6, particularly showing a lip 17A on the recess 17.
Figure 8:
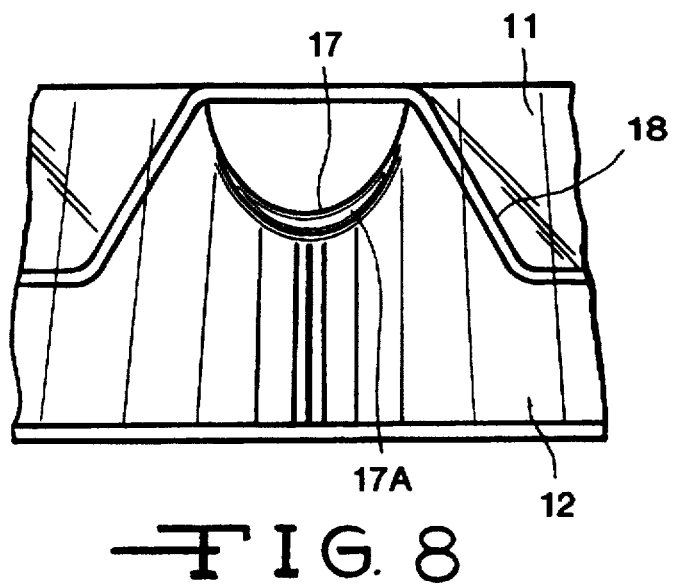
FIG. 8 is a partial front view of the recess 17 and opening 18 showing the lip 17A.
Figure 9:
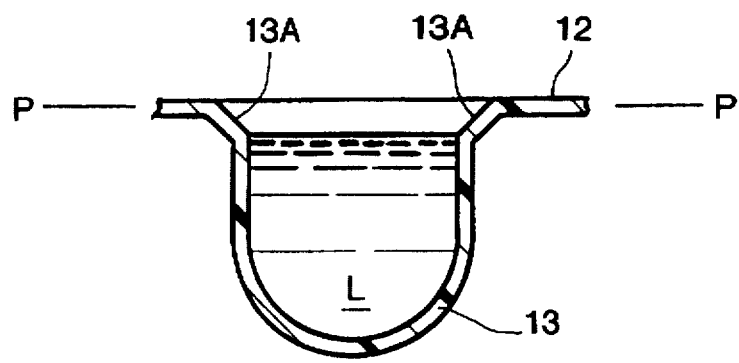
FIG. 9 is a partial cross-sectional view of the well 13 as shown in FIG. 6.
Figure 10:
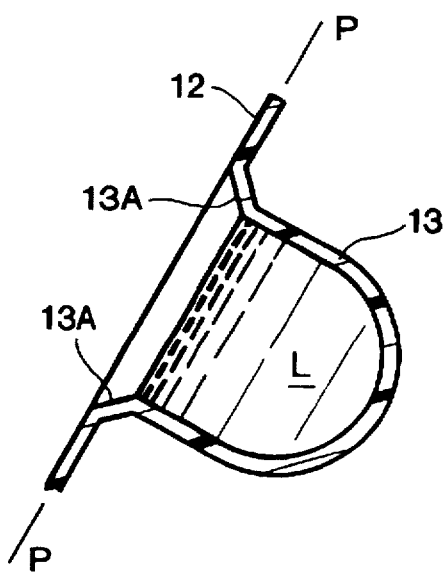
FIG. 10 is a partial enlarged cross-sectional view of the well 13 of FIG. 9 which is tilted.

FIGS. 1 to 10 show various aspects of microorganism culture tray 10, including a transparent cover 11 and integral base 12. The base 12 includes wells 13 with a chamfered opening 13A at an angle from the planar surface P—P shown in FIGS. 9 and 10. The angle is preferably about 45°. The liquid L is retained in the well 13 more readily when the base 10 is tilted as shown in FIG. 10 to drain off excess liquid culture medium. As shown in FIGS. 1 and 2 the wells 13 form concentric circular rows on the planar surface P—P around longitudinal axis A—A (FIG. 3). A first polygonal wall, preferably an octagonal wall 14, as shown in FIGS. 2 and 3 is provided around the axis A—A with flat portions 14A. A second polygonal wall 15 is provided around the axis A—A so that they join in an inverted "V" as shown in FIG. 6 with corresponding flat portions 15A. A flange 16, which is preferably also polygonal at its extreme edge, extends from the second polygonal wall 15. A recess 17 is provided in both walls 15 and 16 at an intersection of two flat portions 14A and 15A (FIG. 1) which allows the liquid culture medium L to be drained from the wells 13 when the planar surface P—P is tilted at an angle of less than 90° as shown in FIG. 6. The liquid culture medium L stays in the wells to be incubated with a microorganism.

The transparent cover 11 conforms to the second polygonal wall 15 of the base 12. In the preferred form, the cover 11 has eight (8) flat portions, conforming to the flat portions 14A and 15A. The cover 11 is provided with an opening 18 which in a first portion allows fluid to be drained through the recess 17 (FIGS. 1, 3, 4, 6, 7 and 8), and in a second portion covers the recess. The flat portions 14A and 15A on the base 12 provide for these two positions without any potential for a mismatch. Thus, the polygonal shape of at least the second polygonal wall 15 is important. The first polygonal wall 14 is preferably the same shape as the second polygonal wall. The hexagonal shape of the outer edge of the flange 16 is preferred so that the trays 10 can be assembled in a closely packed relationship on a table top or the like.

The recess 17 has a protruding lip 17A which aids in preventing drips when culture medium is drained, as shown in FIG. 6. This aids in preventing laboratory contamination. Typically the culture medium is provided in the tray 10 admixed with a sample suspected of being contaminated with a microorganism. Culture medium such as described in U.S. patent application Ser. No. 08/753,715, filed Nov. 27, 1996 can be used in the tray 10.

The base 12 and cover 11 can each be vacuum molded. The preferred material for the cover 11 is polyvinylchloride (PVC). The base 12 is coex polystyrene, which does not interfere with the culturing of the microorganisms.

EXAMPLE

Each tray 10 preferably contains 84 fixed "wells" which can hold approximately 0.06 mL of media, e.g., *E. coli/T. coliform* media. These fixed wells serve an analogous function to the 84 individual culture "tubes" used in traditional most probable number (MPN) methods, i.e., equivalent to the 84 tube MPN at a single level. The method is based on the same assumptions as for traditional MPN (tube) method: (1) the sample is prepared in such a manner that the bacteria are distributed randomly; (2) the bacteria are separate, not clustered together, and do not repel each other; and (3) the growth medium and conditions of incubation have been chosen so that every well that contains even one viable organism will produce detectable growth. The number of wells producing the desired reaction (.e.g. color change, fluorescence) represents an estimate of the original, undiluted concentration of bacteria in the sample in the same manner as the corresponding number of tube would in the MPN method. The mathematical relationship as derived from the MPN method is as follows:

$$MPN = 2 \{N \, Log_e[N/(N-x)]\}$$

where N=number of tubes or wells, i.e., 84 for the tray 10 x=number of colored and/or fluorescent wells

2=factor—as ½ sample poured off from the tray 10

In practice, 10 mL of media/sample mixture is added to the tray and the liquid distributed evenly over the fixed wells prior to pouring off the excess liquid (approximately 5 mL). The tray 10 is inverted and placed in an incubator at a specified temperature for a period of time. In the case of *E. coli/T. coliforms*, the tray 10 is incubated at 37° C. for 24 hours. Wells that contain members of the Enterobacteriaceae ("coliforms") appear red to purple and those that are red and fluoresce when exposed to U.V. light (365 nm) are *E. coli* Biotype I. The number of colored wells which also fluoresce are used to determine the number of *E. coli* in the sample using the aforementioned calculation.

It is intended that the foregoing description be only illustrative of the present invention and that the present invention be limited only by the hereinafter appended claims.

We claim:

1. A microorganism culture tray which comprises:
   (a) an integral base with (i) a planar surface having multiple concentric circular rows of wells around a longitudinal axis for containing a liquid culture medium and the microorganisms, (ii) a first wall projecting from the planar surface above the wells around the axis with flat portions, (iii) a second regular polygonal wall with flat portions connected to the first wall to form an inverted V intersection above the wells and planar surface and extending below the planar surface below the wells, and (iv) an outwardly extending flange from the second wall upon which the base rests; and (v) a recess in both of the walls at intersections of two of the flat portions of the walls which allows the liquid culture medium to be drained from the planar surface when the planar surface is tilted at an angle less than 90°; and (b) a transparent integral transparent cover having flat portions defining a wall of the cover conforming to the second wall of the base wherein an intersection of two of the flat portions of the cover define an opening which exposes the recess when the cover is in one position and covers the recess when the cover is in another position on the base.

2. The tray of claim 1 wherein the recess has a lip on the second wall.

3. The tray of any one of claims 1 or 2 wherein the cover has a circular depression towards the wells to allow easy visualization of the wells.

4. The tray of any one of claims 1 or 2 wherein the wall of the cover has an outwardly extending flange which is parallel to the flange of the base.

5. The tray of any one of claims 1 or 2 wherein the outwardly extending flange is a first flange and wherein the opening in the cover has an outwardly extending second flange which is continuous with the first flange.

6. The tray of any one of claims 1 or 2 wherein the wells have a circular rim which is enlarged around a circumference of the well which is circular.

7. The tray of claim 1 wherein the recess has a lip on the second wall; wherein the cover has a circular depression towards the wells to allow easy visualization of the wells; wherein the wall of the cover has an outwardly extending flange which is parallel to the flange of the base; wherein the opening in the cover has an outwardly extending second flange which is continuous with the flange on the cover; and wherein the wells have a circular rim which is enlarged around a circumference of the well which is circular.

8. Tray of claim 1 wherein the base and cover are vacuum formed.

9. The tray of claim 1 wherein the first and second walls are both hexagonal.

10. A method for culturing a bacterium which comprises:
    (a) introducing a bacterium into a tray which comprises: an integral base with (i) a planar surface having multiple concentric circular rows of wells around a longitudinal axis for containing a liquid culture medium and the microorganisms, (ii) a first regular polygonal wall projecting from the planar surface above the wells around the axis with eight flat portions, (iii) a second regular polygonal wall with eight flat portions connected to the first wall to form an inverted V intersection above the wells and planar surface and extending below the planar surface below the wells, and (iv) an outwardly extending flange from the second wall upon which the base rests; and (v) a recess in both of the walls at intersections of two of the flat portions of the walls which allows the liquid culture medium to be drained from the wells and planar surface when the planar surface is tilted at an angle less than 90°; and a transparent integral transparent cover having eight flat portions defining a wall of the cover conforming to the second wall of the base wherein an intersection of two of the flat portions of the cover define an opening which exposes the recess when the cover is in one position and covers the recess when the cover is another position on the base;

(b) culturing the bacterium in the tray so that the bacterium is visible.

11. The method of claim 10 wherein the base is white and the bacterium is visualized on the base as a result of the culturing.

* * * * *